(12) United States Patent
Choi et al.

(10) Patent No.: US 10,393,744 B2
(45) Date of Patent: Aug. 27, 2019

(54) PEPTIDES FOR TARGETING COLORECTAL CANCER, AND MEDICAL USE THEREOF

(71) Applicant: UNIVERSITY OF ULSAN FOUNDATION FOR INDUSTRY COOPERATION, Ulsan (KR)

(72) Inventors: Eun Kyung Choi, Seoul (KR); Seong-Yun Jeong, Yongin-si (KR); Si Yeol Song, Seoul (KR); Kyoung Jin Lee, Seoul (KR); Jinhyang Choi, Seoul (KR); Jaesook Park, Seoul (KR); Seok Soon Park, Bucheon-si (KR); Jae Hee Lee, Goyang-si (KR)

(73) Assignee: UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 63 days.

(21) Appl. No.: 15/527,716

(22) PCT Filed: Jul. 29, 2015

(86) PCT No.: PCT/KR2015/007942
§ 371 (c)(1),
(2) Date: May 18, 2017

(87) PCT Pub. No.: WO2016/080632
PCT Pub. Date: May 26, 2016

(65) Prior Publication Data
US 2017/0328906 A1    Nov. 16, 2017

(30) Foreign Application Priority Data

Nov. 18, 2014 (KR) .......................... 10-2014-0160817
Jul. 28, 2015 (KR) .......................... 10-2015-0106580

(51) Int. Cl.
| | | |
|---|---|---|
| *A61K 49/00* | (2006.01) |
| *G01N 33/574* | (2006.01) |
| *A61K 51/08* | (2006.01) |
| *G01N 33/58* | (2006.01) |
| *A61K 47/50* | (2017.01) |
| *A61K 47/00* | (2006.01) |
| *C07K 14/00* | (2006.01) |
| *G01N 33/00* | (2006.01) |

(52) U.S. Cl.
CPC .......... *G01N 33/574* (2013.01); *A61K 47/50* (2017.08); *A61K 49/0004* (2013.01); *A61K 51/08* (2013.01); *G01N 33/57419* (2013.01); *G01N 33/58* (2013.01); *A61K 47/00* (2013.01); *A61K 49/00* (2013.01); *C07K 14/00* (2013.01); *G01N 33/00* (2013.01)

(58) Field of Classification Search
None
See application file for complete search history.

(56) References Cited

U.S. PATENT DOCUMENTS

| | | | |
|---|---|---|---|
| 8,691,189 B2 | 4/2014 | Guan et al. | |
| 8,846,623 B2 | 9/2014 | Yu et al. | |
| 2003/0154513 A1* | 8/2003 | Eenennaam | ......... C12N 9/1007 800/281 |
| 2013/0137603 A1 | 5/2013 | Lee et al. | |

FOREIGN PATENT DOCUMENTS

| | | | |
|---|---|---|---|
| KR | 10-2009-0063924 A | 6/2009 | |
| KR | 10-2013-0046457 A | 5/2013 | |
| KR | 1020130040493 | * | 4/2014 |

OTHER PUBLICATIONS

Colorectal Cancer definition (retrieved from https://www.ccalliance.org/colorectal-cancer-information/what-is-colorectal-cancer on Nov. 29, 2018, 4 pages). (Year: 2018).*
English translation of Choi et al. KR 1020130040493 Apr. 2014 (retrieved from http://engpat.kipris.or.kr/pmt/patent/ on Nov. 29, 2018, 18 pages) (Year: 2018).*
International Search Report for PCT/KR2015/007942 dated Oct. 16, 2015 from Korean Intellectual Property Office.
Wei, W. et al., "Screening and identifying of homing peptides to bladder cancer BIU-87 cells in Chinese", Chinese Journal of Cancer Biotherapy, vol. 20, No. 5, pp. 515-521 (2013).

* cited by examiner

*Primary Examiner* — Karlheinz R. Skowronek
*Assistant Examiner* — Ronald T Niebauer
(74) *Attorney, Agent, or Firm* — Revolution IP, PLLC

(57) ABSTRACT

Provided is a peptide for targeting colorectal cancer, a composition for diagnosing radioresponsiveness-dependent prognosis of colorectal cancer using the peptide, and a drug delivery use of the peptide, wherein a functional peptide capable of targeting cancer has been discovered so as to implement personalized diagnosis and treatment for individual patients having cancer, in consideration of problems occurring during treatment in which treatment cases of respective patients differ due to different therapeutic responses resulting from genetic differences in the individual patients.

10 Claims, 9 Drawing Sheets

Specification includes a Sequence Listing.

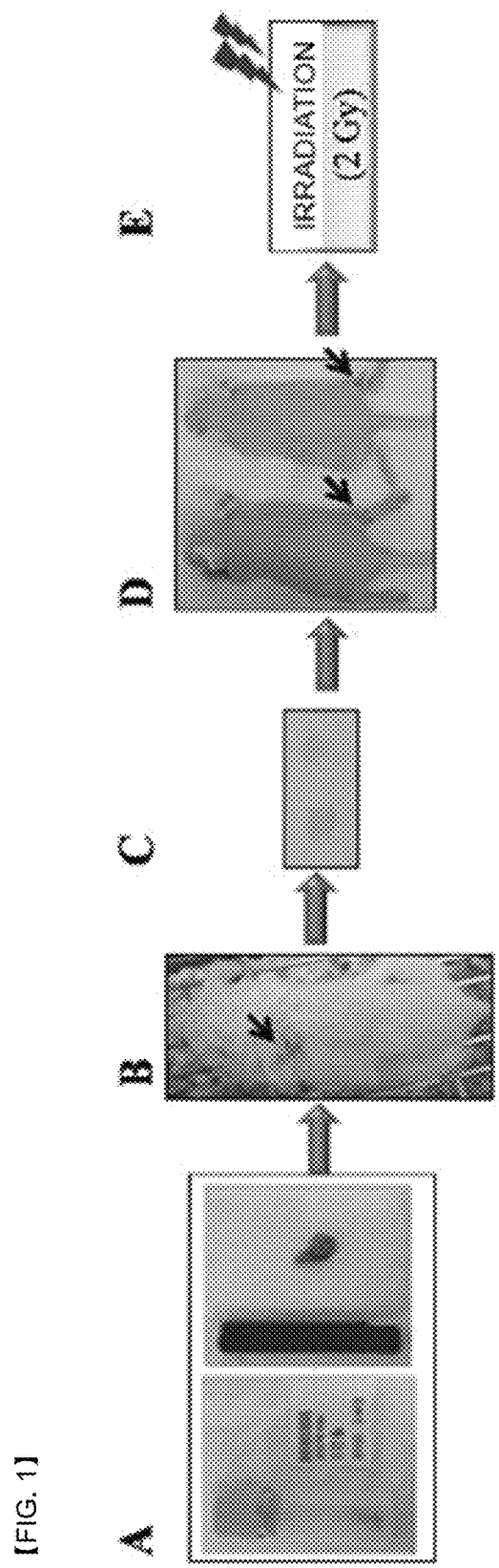
[FIG. 1]

[FIG. 2]
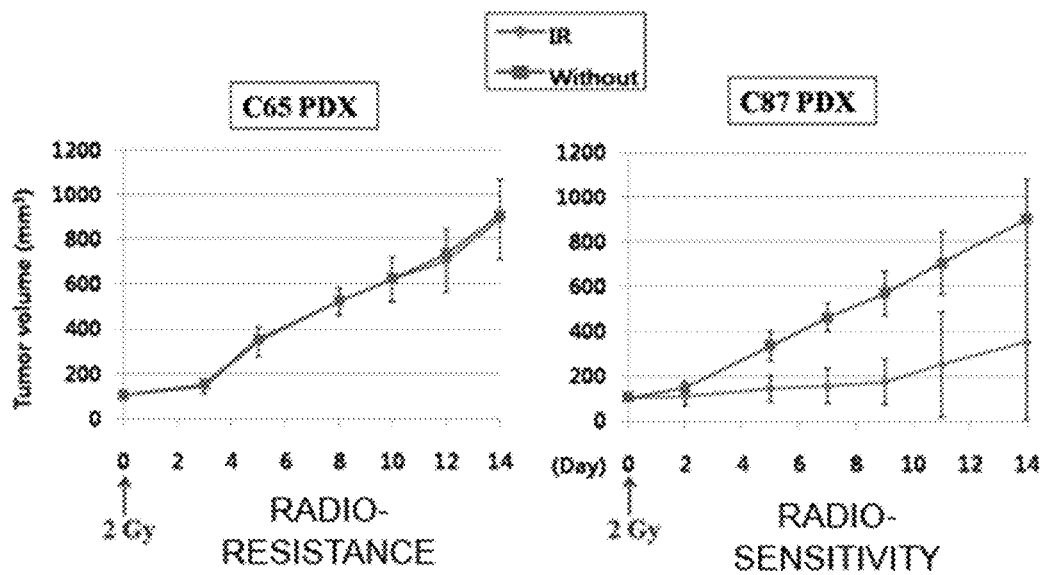
[FIG. 3]
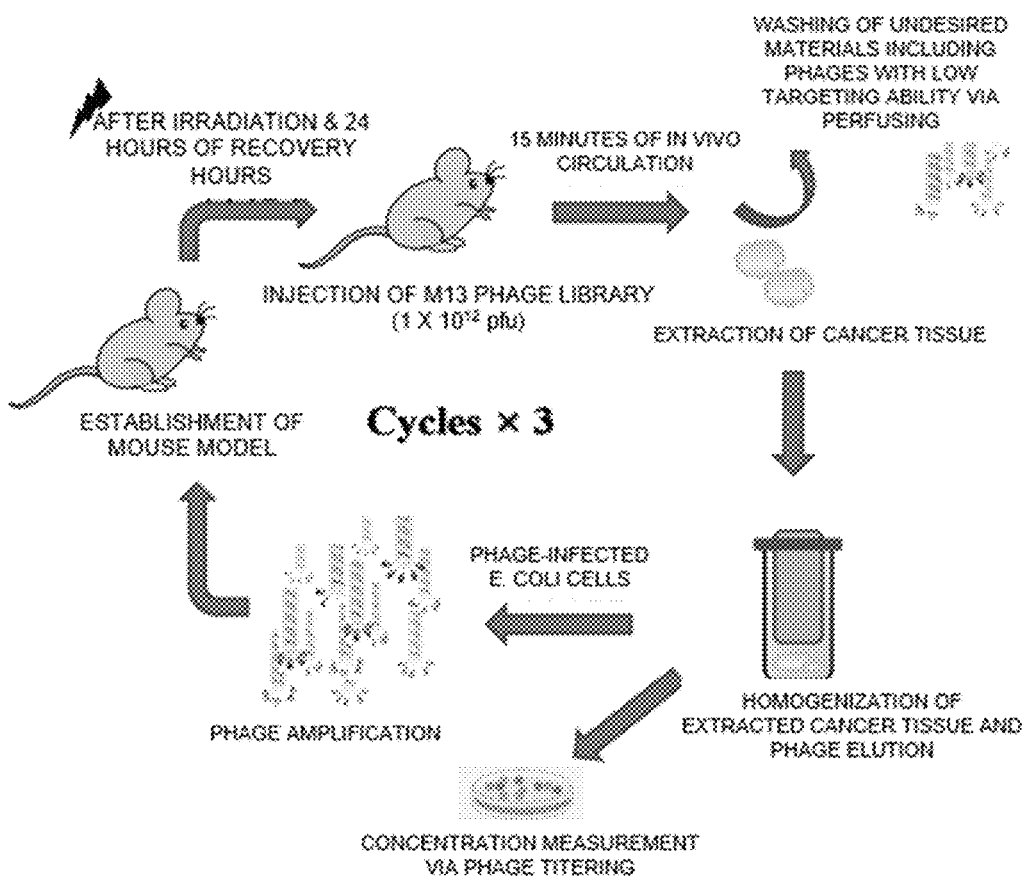

[FIG. 4]
RADIO-RESISTANCE CASE (C65)
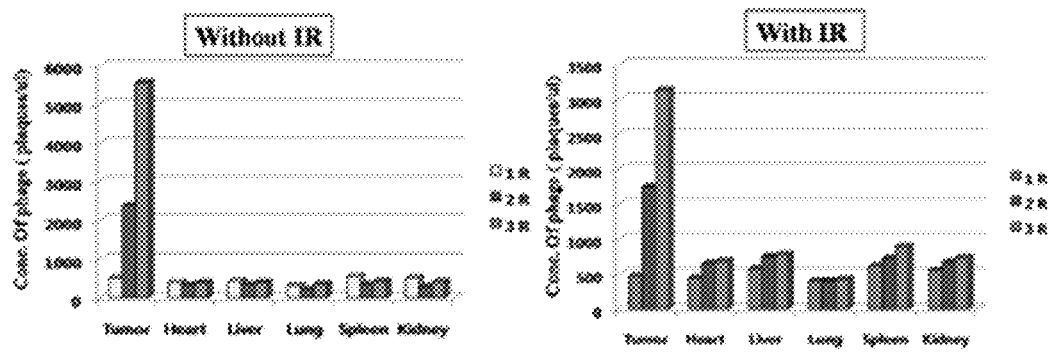
RADIO-SENSITIVE CASE (C87)
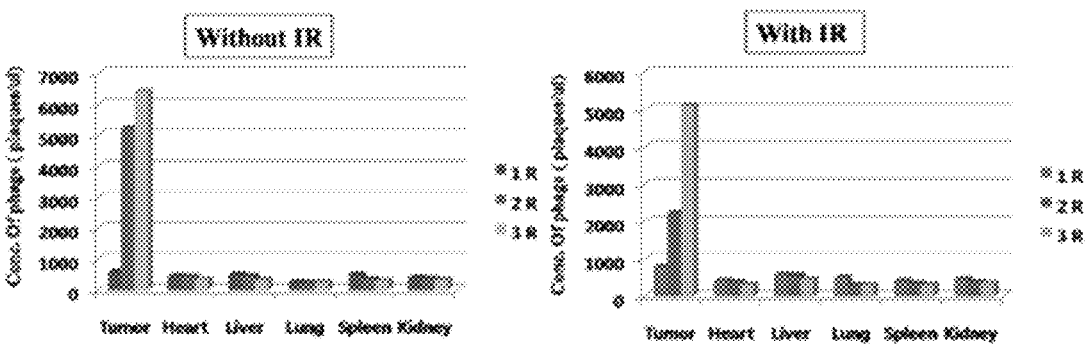

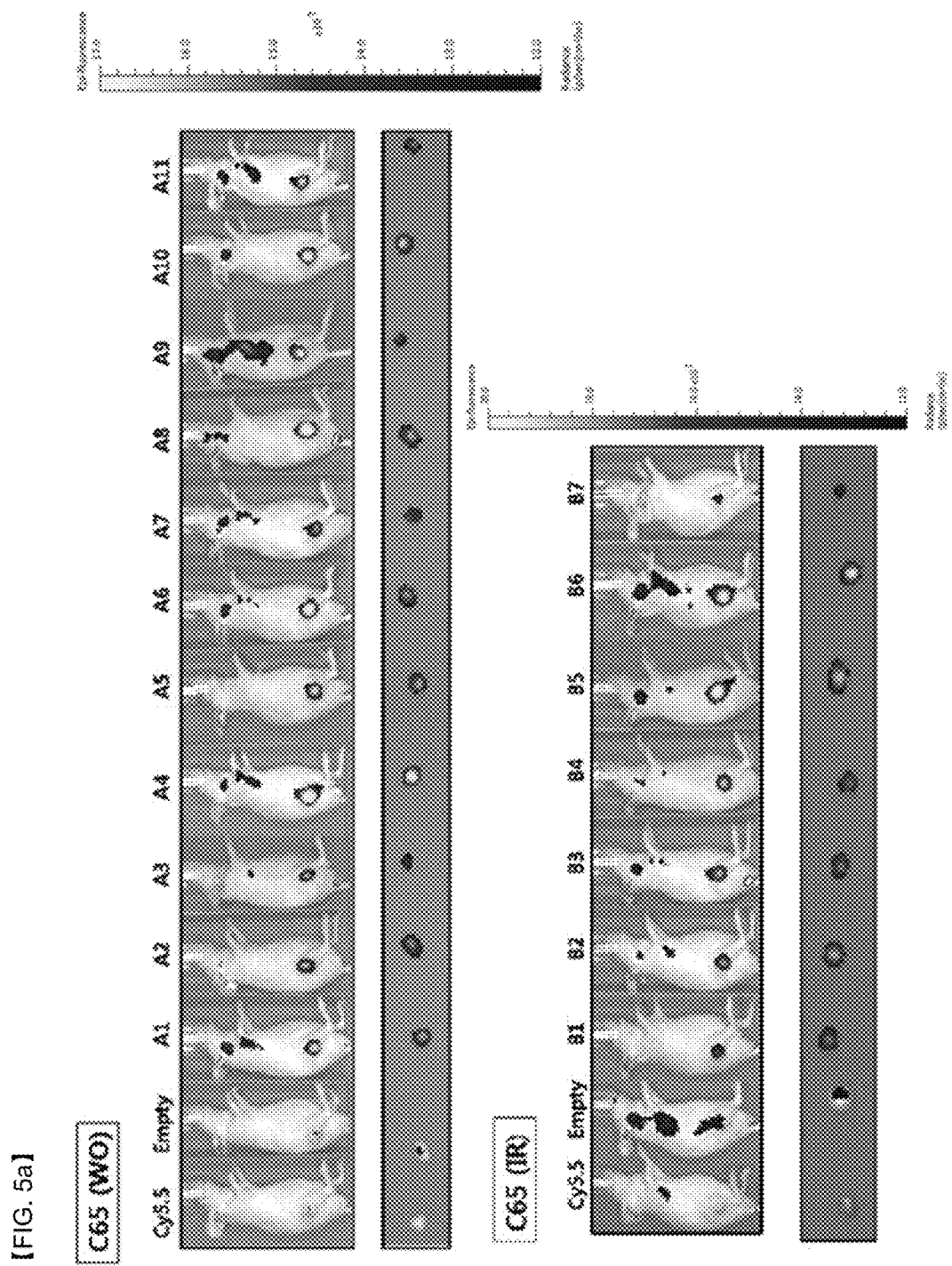
[FIG. 5a]

[FIG. 5b]
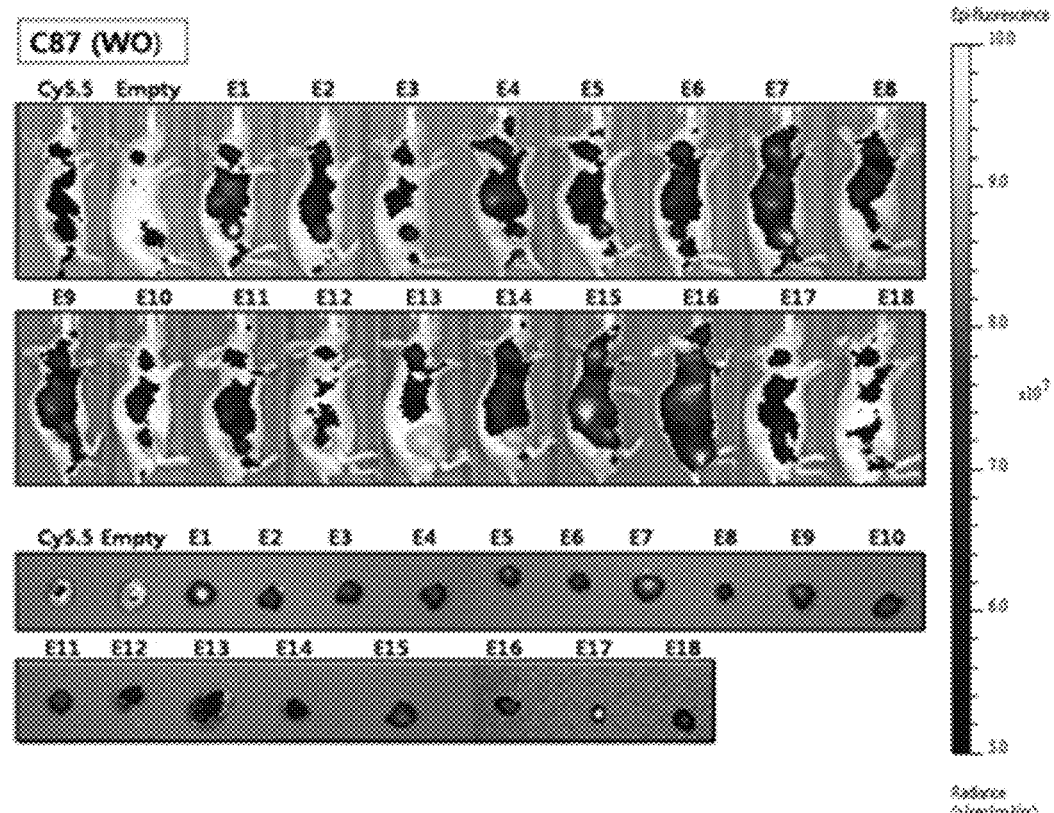
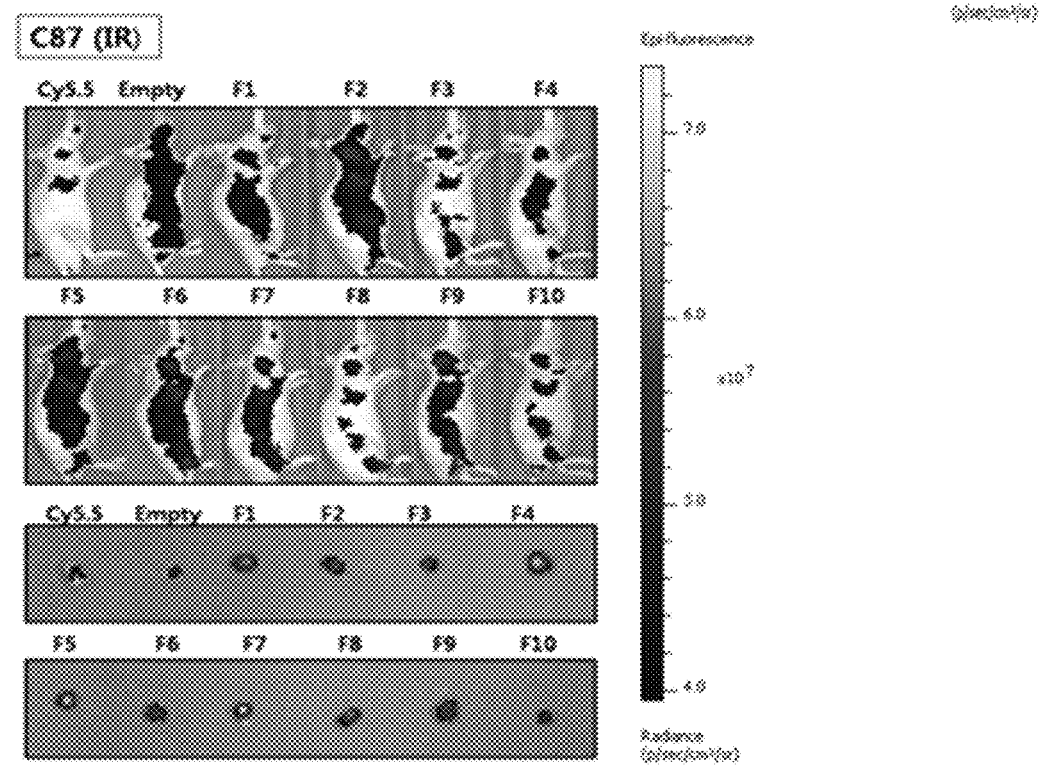

[FIG. 6]
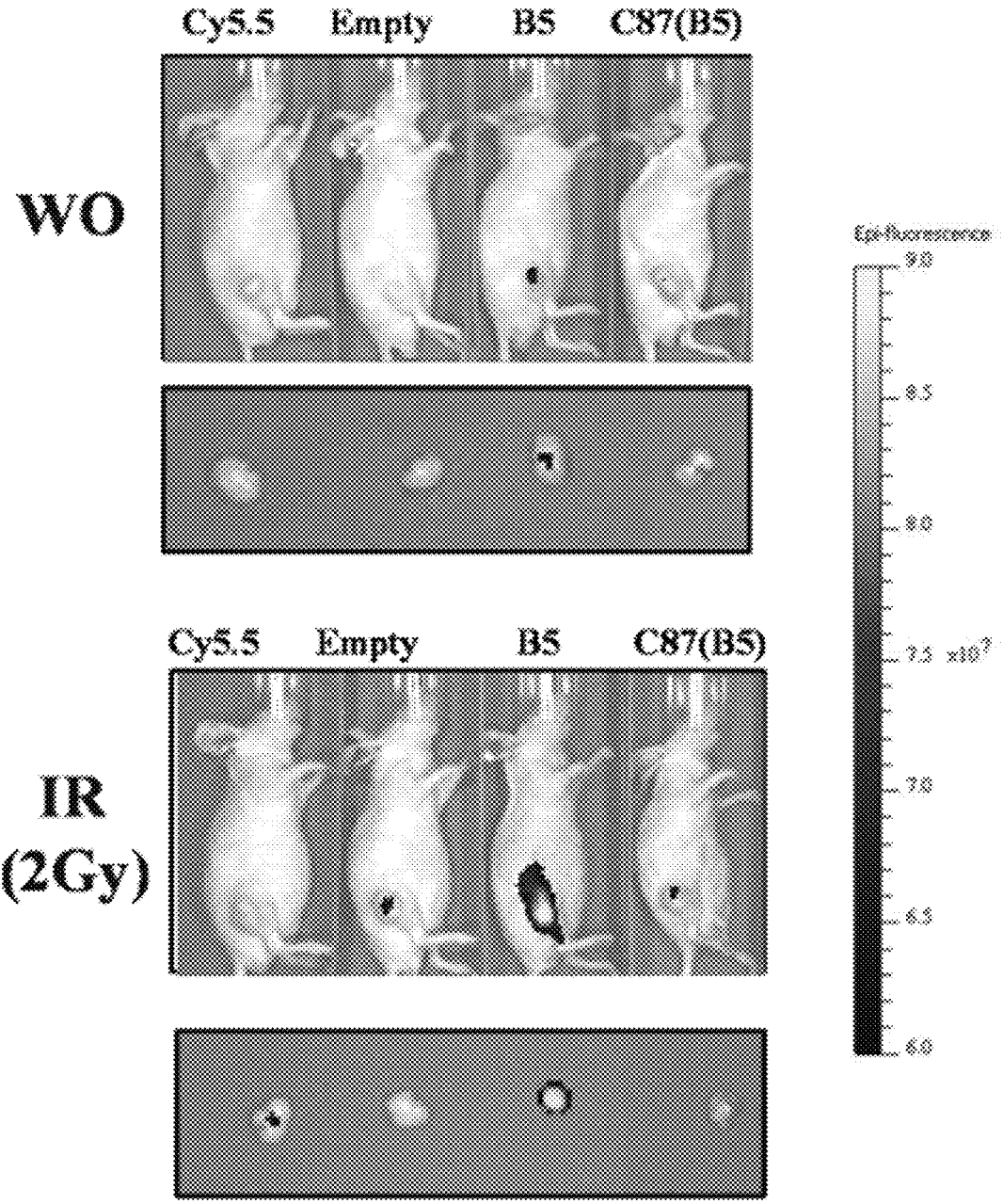

[FIG. 7]
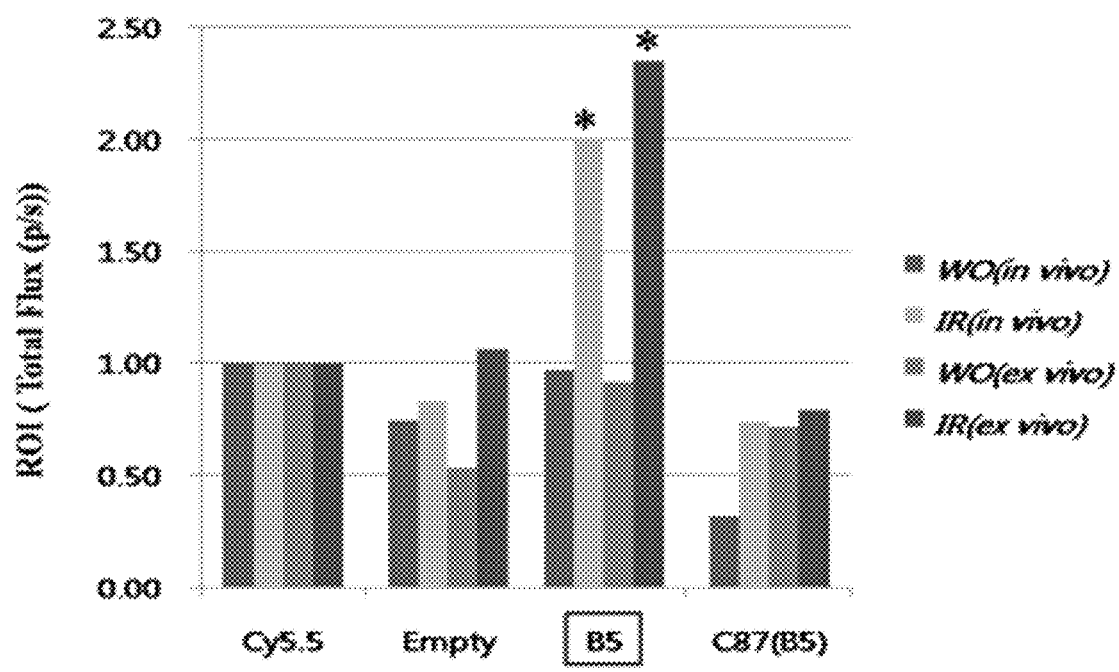

[FIG. 8]
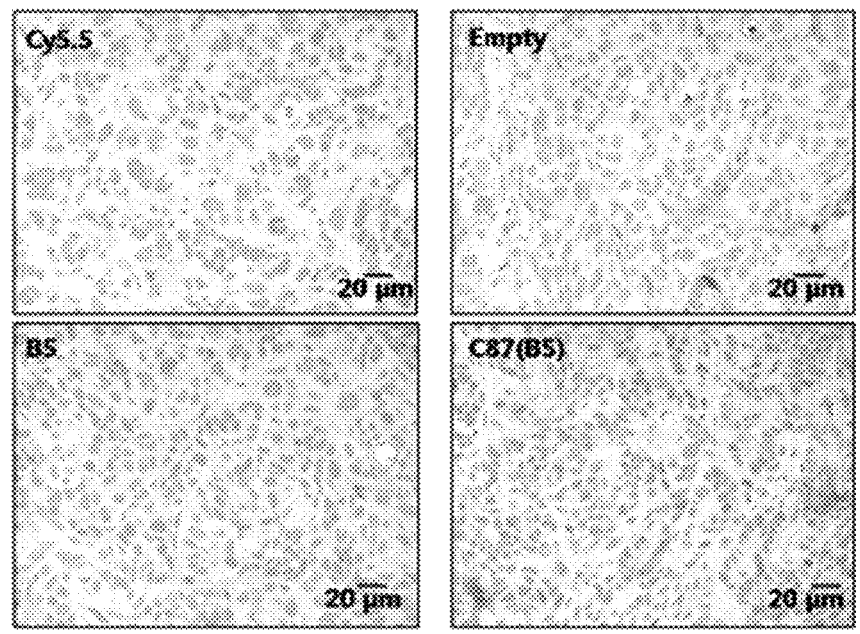
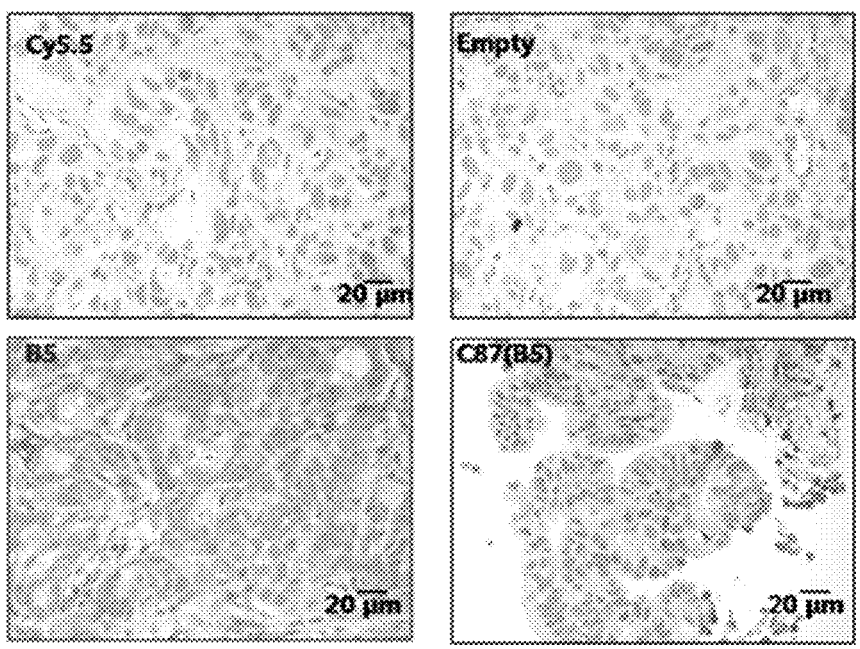

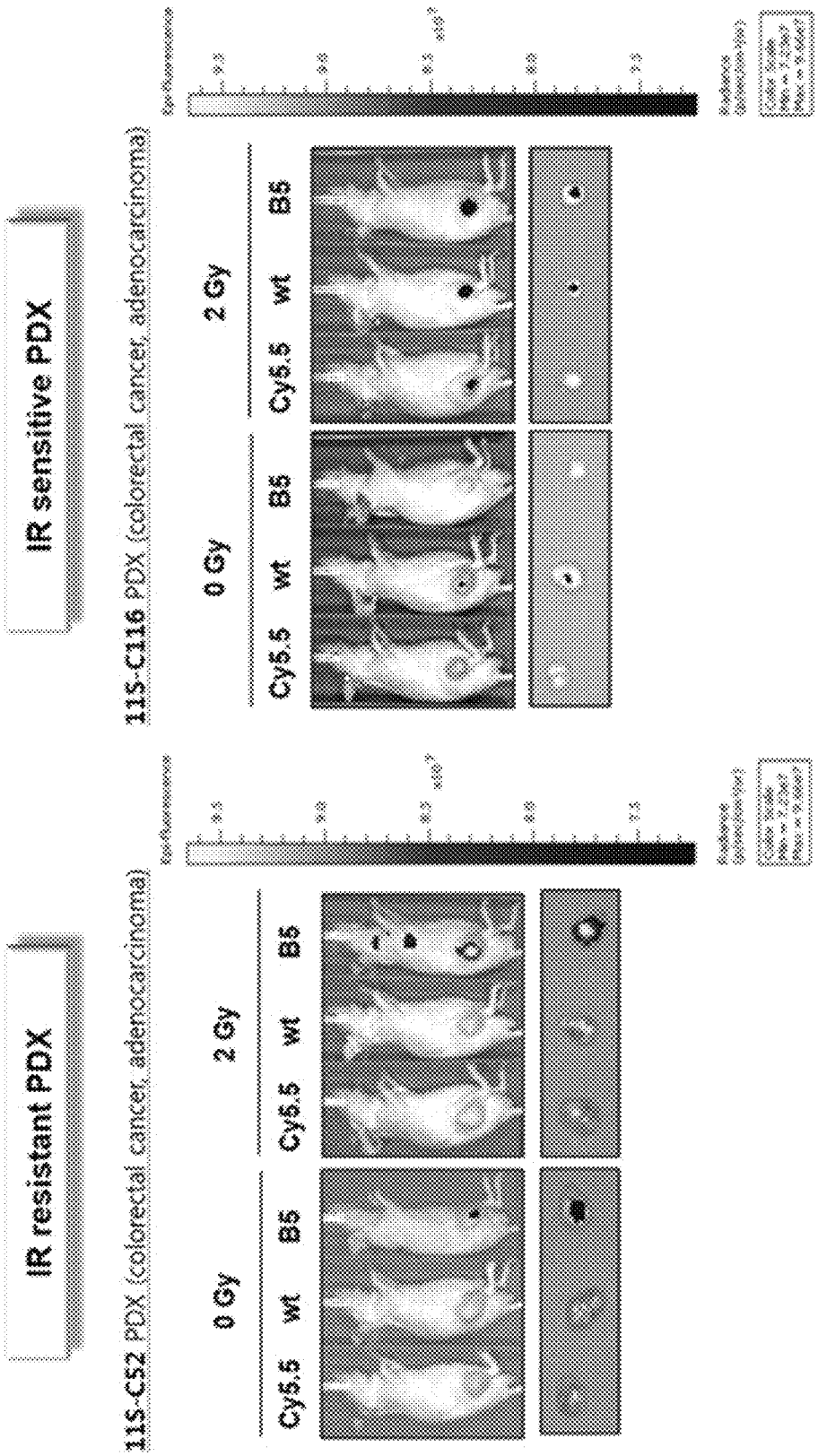
[FIG. 9]

```
                        SEQUENCE LISTING

<160> NUMBER OF SEQ ID NOS: 40

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Ser His Met Glu Tyr Pro Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Asn Thr Gly Ser Pro Tyr Glu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Ser Asn Val Tyr Asp His Asn
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Ser Thr Glu His Thr Arg Ser
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Ser Trp Gly Asp Arg Ile Leu
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Leu Gln Pro Lys Ala Ser Gln
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ala Ser Lys Ser Thr His Asp
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Asp Val Ser Gly Asn Trp
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Asp Leu Leu His Arg Gly Ala
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Met Ala Arg Tyr Met Ser Ala
1               5
```

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Asn Thr Trp Met Lys Ser Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Ser Thr Met Asn Gly Lys Val
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Thr Val Arg Ser Ser Ala Glu
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Val Pro Ser Gln Lys Ser Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Thr Pro Ser Phe Ser Lys Ile
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Gly Tyr Ser Ser Phe Asn Arg
1               5

```
<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Leu Lys Leu Gly Glu Lys Trp
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Val Gln Met Pro Ala His Ser
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Gly Gly Asn Ser Asn Gln Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Thr Ala Phe Ser Leu Gly Lys
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Gln Gln Thr Lys Asn Tyr Tyr
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Ala Ile Lys Asn Thr Lys Ser
1               5

<210> SEQ ID NO 23
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Thr Val Arg Thr Ser Ala Val
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Leu Thr Gly Ser Val Asn Lys
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Met Asn Phe Ile Gln Lys Asn
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Asp Glu Thr Ser Gly Gln Ile
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Lys Ile Ser Leu Pro His Asn
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

Ala Phe Lys Ser Pro Ser Gly
1               5

<210> SEQ ID NO 29
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 29

Leu Lys Thr Ser Gly Thr Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Arg Ser Thr Gly Ser Ser Cys
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Tyr Val Ser Lys Asn Asn Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

His Lys Thr Glu His Arg Ser
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide

<400> SEQUENCE: 33

Lys Leu Thr Gln Met Met
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34

Ser Phe Phe Pro Phe Ser Thr
1               5

<210> SEQ ID NO 35
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 35

Asp Asn Ser Lys Leu Val Glu
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

Gln Leu Trp Gln Lys Glu Gln
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

Leu Gly Ser Val Gly Arg Asp
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

Gly Gln Ser Gly Ala Arg Phe
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Asn Gly Asn Ser Asn Thr Leu
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Thr Asn Pro Tyr Pro Leu Asp
1               5
```

PEPTIDES FOR TARGETING COLORECTAL CANCER, AND MEDICAL USE THEREOF

CROSS REFERENCE TO PRIOR APPLICATIONS

This application is a National Stage Application of PCT International Patent Application No. PCT/KR2015/007942 filed on Jul. 29, 2015, under 35 U.S.C. § 371, which claims priority to Korean Patent Application Nos. 10-2014-0160817 filed on Nov. 18, 2014, and 10-2015-0106580 filed on Jul. 28, 2015, which are all hereby incorporated by reference in their entirety.

TECHNICAL FIELD

The present invention relates to a peptide for targeting colorectal cancer, a composition for diagnosing prognosis of colorectal cancer based on radioresponsiveness using the peptide, and drug delivery use of the peptide.

BACKGROUND ART

Cells which are the smallest unit of the human body maintain the balance of cell number by cell division upon intracellular regulatory functions, cell growth, and cell death and disappear, when cells are normal. If the cells are damaged by any cause, cells may be recovered by treatment to thereby serve as normal cells. However, if cells are not recovered, cells die by themselves. A condition in which abnormal cells that do not control proliferation and inhibition thereof for a variety of reasons are excessively proliferated and also cause tumefaction and destruction of normal tissues by invading surrounding tissues and organs is defined as cancer. As such, cancer refers to cell proliferation that is not inhibited, and cancer destroys the structure and function of normal cells and organs. In this regard, it is significantly important to diagnose and treat cancer.

However, there are problems during treatment in which treatment cases of respective patients differ due to different therapeutic responses resulting from genetic differences in the individual patients having cancer. Thus, in order to effectively treat cancer patients, it is required to develop a functional targeting agent capable of targeting tumor microenvironment, which depends on radioresponsiveness, and a biomarker. Accordingly, it is possible to establish personalized diagnosis and treatment for individual patients.

In addition, drug delivery systems or targeted therapies that selectively deliver drugs to cancer cells and cancer tissues are technologies that have received much attention, because even if the same amount of an anticancer agent is used, drug efficacy may be increased while side effects of drugs on normal tissues may be significantly reduced at the same time. In addition, when such technologies are applied to gene therapy, selective delivery of virus to cancer cells can increase treatment efficacy and reduce severe side effects. For this purpose, antigens that are mainly specific to tumor cells and antibodies that target such antigens have been developed up to date. However, in the case of antibodies, there are problems including concerns of immune response and low efficiency of penetration into tissues. In the case of peptides, a molecular weight thereof is so small that there is less concern of an immune responses and the penetration of peptides into tissues is easy. Therefore, if cancer-targeting peptides are coupled with existing anticancer drugs, such resulting products can be utilized as intelligent drug vehicles that selectively deliver drugs to tumors.

DETAILED DESCRIPTION OF THE INVENTION

Technical Problem

The present invention, unlike screening methods that have been studied at the existing cell culture levels, establishes mouse models transplanted with a cancer tissue of an actual human, to thereby divide them into an irradiated population and a non-irradiated population as a control group. In particular, each population is divided into a radio-sensitive population and a radio-resistant population, and a method of screening a peptide that specifically binds to each population above is disclosed to provide a novel peptide for targeting colorectal cancer and a medical use of such a novel peptide.

Technical Solution

To solve the technical problem above, the present invention provides a peptide for targeting colorectal cancer and a polynucleotide encoding the peptide, the peptide including an amino acid sequence selected from the group consisting of SEQ ID NOs: 1 to 40.

In an embodiment, the present invention provides a peptide for targeting colorectal cancer, the peptide including an amino acid selected from the group consisting of SEQ ID NOs: 12 to 15, 17, and 33 to 40 and being specific to a colorectal cancer tissue that is irradiated.

In an embodiment, the present invention provides a composition including the peptide for diagnosing colorectal cancer and a composition including the peptide for diagnosing radio-reactive colorectal cancer.

In an embodiment, the present invention provides a composition including the peptide for delivering a drug.

Advantageous Effects of the Invention

The present invention relates to a peptide for targeting colorectal cancer, a composition for diagnosing prognosis of colorectal cancer using the peptide, and a drug delivery use of the peptide. Considering problems during treatment in which treatment cases of respective patients differ due to different therapeutic responses resulting from genetic differences in the individual patients having cancer, a functional peptide capable of targeting cancer has been discovered so as to establish personalized diagnosis and treatment for individual patients. Animal models similar to cancer microenvironments of actual patients having cancer are prepared and divided into irradiated populations and non-irradiated populations as a control group, to thereby test target efficiency for respective peptides that are selected by screening peptides specifically binding to the respective populations. As such, the present invention can be finally utilized in the technical development of image diagnosis for predicting responsiveness to radiotherapy, and accordingly, the development of customized targeted therapeutic agents.

DESCRIPTION OF THE DRAWINGS

FIG. 1 is an image showing a method of establishing an irradiated animal model after transplanting an actual patient's colorectal cancer tissue into a mouse according to Example 1 of the present invention, and also showing confirmation results of the established animal model. FIG.

1A shows a patient's colorectal cancer tissue distributed from the Bio Research Center (BRC, Korea), FIG. 1B shows a NOD/SCID mouse that undergoes heterotrophic transplantation into the flanks of the mouse, FIG. 1C shows a cancer tissue cut into pieces each having a size of 3×3 mm to be used for subculturing, when the size of the cancer tissue of FIG. 1B is increased up to 500 mm$^3$, FIG. 1D shows a mouse model prepared in a way that a nude mouse is anesthetized via intraperitoneal injection and undergoes heterotrophic transplantation of one piece of the cut tissues subcutaneously on the right thigh of the mouse, and FIG. 1E shows local irradiation of 2 grays (Gy) of radiation over the thigh portion where the cancer cell is formed, when the size of the cancer tissue is increased up to 250 mm$^3$. Here, a control group is not subjected to irradiation.

FIG. 2 shows graphs of cancer proliferation curves obtained depending on whether a mouse transplanted with a patient's cancer tissue is irradiated, so that the mouse model can be classified based on reactivity by irradiation according to Example 2. As a result of completing and confirming the corresponding proliferation curves, case C65 refers to a radio-resistant mouse while case C87 refers to a radio-sensitive mouse.

FIG. 3 shows a biopanning scheme for identifying a sequence of a peptide, which targets a colorectal cancer tissue of an in vivo patient, in each population using an M13 phage display method according to embodiments of the present invention FIG. 4 shows the results of comparing phage concentrations obtained by eluting phages after extracting heart, lung, liver, spleen, kidney, and tumor during biopanning process performed three times.

FIG. 5 shows the results confirming that, after injecting a peptide phage labeled with a Cy5.5 fluorescent probe into the mouse model of each population, the radio-resistant mouse (case C65; FIG. 5A) on the 7$^{th}$ day of the injection and the radio-sensitive mouse (case C87; FIG. 5B) on the 11$^{th}$ day of the injection were to be specifically bind to the cancer tissue in vivo based on images.

FIG. 6 shows cross-validation results regarding specific binding of a B5 peptide sequence only to an irradiated population in radio-resistant case, by comparison with other control groups.

FIG. 7 shows results obtained by which ROI values are calculated and standardized based on the cross-validation results regarding the B5 peptide.

FIG. 8 shows results that verify excellent targeting ability of the B5 peptide through tissue immunohistochemistry.

FIG. 9 shows colorectal cancer tissues of a patient other than the existing radio-sensitive/radio-resistant colorectal cancer tissues of patients according to Example 7 of the present invention, and provides results for confirming selective targeting ability of the B5 peptide in each population of the radio-sensitive case the ratio-resistant patient case depending on the presence of irradiation.

BEST MODE

The present invention provides a peptide for targeting colorectal cancer, the peptide including an amino acid sequence selected from the group consisting of SEQ ID NOs: 1 to 40. The above-mentioned amino acid sequences are shown in Tables 1 and 2.

The peptide of the present invention is a low-molecular weight peptide consisting of 7 amino acids. Such a low-molecular weight peptide is small in size so that it can be stabilized three-dimensionally. In addition, a low-molecular weight peptide has the advantage of being able to easily pass through a membrane and to recognize a target molecule deep in tissues. Since the stability of the low-molecular weight peptide of the present invention is secured through local injection and the immunoreactivity can be minimized, there is an advantage that cancer can be diagnosed early. In addition, the mass production of the low-molecular weight peptide of the present invention is relatively easy compared that of an antibody, and the toxicity of the low-molecular weight peptide of the present invention is weak.

In addition, the low-molecular weight peptide of the present invention is has an advantage of a strong binding force to a target material compared to an antibody, and do not undergo denaturation during thermal/chemical treatment. In addition, due to a small molecular size, the low-molecular weight peptide can be used as a fused protein as being attached to other proteins. In detail, the low-molecular weight peptide can be also used as being attached to a high-molecular weight protein chain, and accordingly, can be used as a diagnosis kit and a drug delivery carrier.

The low-molecular weight peptide of the present invention can be easily prepared according to the chemical process known in the art (Creighton, Proteins; Structures and Molecular Principles, W. H. Freeman and Co., NY, 1983). As representative methods, liquid or solid phase synthesis, fractional condensation, F-MOC or T-BOC chemical method, or the like may be used (Chemical Approaches to the Synthesis of Peptides and Proteins, Williams et al., Eds., CRC Press, Boca Raton Fla., 1997; A Practical Approach, Athert on & Sheppard, Eds., IRL Press, Oxford, England, 1989), but the method is not limited thereto.

In addition, the low-molecular weight peptide of the present invention can be prepared according to a genetic engineering method. First, according to a conventional method, a DNA sequence encoding the sequence low-molecular weight peptide is prepared. Here, a DNA sequence can be prepared by PCR amplification using an appropriate primer. Alternatively, according to a standard method known in the art, a DNA sequence can be synthesized using, for example, an automatic DNA synthesizer (manufactured by Biosearch or AppliedBiosystems). Such a synthesized DNA sequence is inserted to a vector including one or more expression control sequences (for example: a promoter, an enhancer, or the like) that are operatively linked to the DNA sequence to control expression of the DNA sequence, and then, a host cell is transformed with a recombinant expression vector prepared therefrom. A resulting transformant is cultured in an appropriate medium under suitable conditions to allow the expression of the DNA sequence, so that substantially pure peptides that are encoded by the DAN sequence are recovered from the culture. Such recovery may be performed according to a method known in the art (for example, chromatography). The term 'substantially pure peptides' used herein refers to peptides that do not substantially include any protein derived from the host.

In addition, the present invention provides a peptide for targeting colorectal cancer, the peptide being specific to an irradiated colorectal cancer tissue and including an amino acid sequence selected from the group consisting of SEQ ID NOs: 12 to 15, 17, and 33 to 40.

In detail, a peptide including an amino acid sequence selected from the group consisting of SEQ ID NOs: 12 to 15, 17, and 33 to 40 specifically binds to a colorectal cancer tissue, in particular, an irradiated colorectal cancer tissue.

The term "target" or "specific" used herein refers to the ability to specifically bind only to a colorectal cancer tissue, especially an irradiated colorectal cancer tissue, without binding to other normal tissues. A colorectal cancer-specific peptide can specifically bind to the inside or outside of a colorectal cancer tissue.

In addition, the present invention provides a peptide for targeting colorectal cancer, the peptide being specific to a radio-resistant colorectal cancer tissue and including an amino acid sequence selected from the group consisting of SEQ ID NOs: 12 to 15.

In addition, the present invention provides a peptide for targeting colorectal cancer, the peptide being specific to a radio-sensitive colorectal cancer tissue and including an amino acid sequence selected from the group consisting of SEQ ID NOs: 33 to 40.

The term "radio-resistance" used herein refers to a condition that is not easily influenced by irradiation and has little change in cell repair or proliferation upon exposure to radiation.

The term "radio-sensitive" used herein refers to a condition that is easily influenced by irradiation and shows changes in cell repair or proliferation upon exposure to radiation.

In the present invention, by determining radio-resistance or radio-sensitivity of target colorectal cancer to be treated with radiation therapy, such determination can be used to decide a radiation dose for the radiation therapy, and accordingly, the efficiency of the radiation therapy and therapeutic results may be improved.

In addition, the present invention provides a polynucleotide encoding an amino acid sequence selected from the group consisting of SEQ ID NOs: 1 to 40.

The term "polynucleotide" used herein refers to a single-stranded or double-stranded polymer of deoxyribonucleotides or ribonucleotides. Such a polynucleotide includes a RNA genome sequence, a DNA sequence (for example, gDNA and cDNA), and a RNA sequence transcribed from the DNA sequence. Unless otherwise mentioned, a polynucleotide includes an analog of a natural polynucleotide.

The polynucleotide includes not only a nucleotide sequence that encodes the peptide for targeting colorectal cancer, but also a sequence complementary to the nucleotide sequence, wherein such a complementary sequence includes not only a perfectly complementary sequence, but also a substantially complementary sequence.

In addition, the polynucleotide may be subjected to modifications. Such modifications include addition, deletion, non-conservative substitution, or conservative substitution of a nucleotide. The polynucleotide encoding the amino acid sequence is also interpreted to include a nucleotide sequence that exhibits substantial identity to the nucleotide sequence. The substantial identity is obtained by aligning the nucleotide sequence with any other sequences to the greatest extent and by analyzing the aligned sequence using algorithms commonly used in the art, and in this regard, the substantial identity may indicate a sequence having at least 80% homology, at least 90% homology, or at least 95% homology with the aligned sequence.

In addition, the present invention provides a composition for diagnosing colorectal cancer, the composition including a peptide including an amino acid sequence selected from the group consisting of SEQ ID NOs: 1 to 40.

In addition, the present invention provides a composition for diagnosing radio-sensitive colorectal cancer, the composition including a peptide being specific to an irradiated colorectal cancer tissue and including an amino acid sequence selected from the group consisting of SEQ ID NOs: 12 to 15, 17, and 33 to 40.

In addition, the present invention provides a composition for diagnosing prognosis of colorectal cancer based on radiation, the composition including a peptide for targeting colorectal cancer, wherein the peptide includes an amino acid sequence selected from the group consisting of SEQ ID NOs: 12 to 15 or 33 to 40.

In detail, the diagnosis of prognosis of colorectal cancer based on radiation refers to determination of radio-resistance or radio-sensitivity of colorectal cancer.

The term "diagnosis" used herein refers to identification of the presence or characteristic of a pathological condition. For the purpose of the present invention, the diagnosis is to identify the presence or characteristic of colorectal cancer.

The diagnosis of colorectal cancer using the peptide of the present invention may be performed by detecting binding of the peptide of the present invention to a corresponding tissue or cell directly obtained from blood, urine, or biopsy.

In addition, to easily confirm, detect, and quantify binding of the peptide of the present invention to the colorectal cancer tissue, the peptide of the present invention can be provided in a labeled state. That is, the peptide provided herein may be linked to a detectable label (for example, via covalent binding or cross-linking). The detectable label may be a chromogenic enzyme (for example, peroxidase and alkaline phosphatase), a radioactive isotope (for example, $^{124}$I, $^{125}$I, $^{111}$In, $^{99m}$TC, $^{32}$P, and $^{35}$S), a chromophore, or a luminescent material or a fluorescent material (for example, FITC, RITC, rhodamine, cyanine, Texas Red, fluorescein, phycoerythrin, or quantum dots).

Similarly, the detectable label may be an antibody-epitope, a substrate, a cofactor, an inhibitor, or a affinity ligand. Such labeling may be performed during the synthesis of the peptide of the present invention, or may be additionally performed on a peptide that is already synthesized. When using a fluorescent material is used as a detectable label, cancer may be diagnosed according to fluorescence mediated tomography (FMT). For example, the peptide of the present invention labeled with a fluorescent material may be circulated into the blood, and the fluorescence by the peptide may be observed by FMT. If fluorescent is observed, it is diagnosed as cancer.

In addition, the present invention provides a composition for delivering a drug, the composition including the peptide for targeting colorectal cancer.

The peptide of the present invention may be used as an intelligent drug delivery vehicle that selectively delivers a drug to a cancer tissue. If the peptide of the present invention is used in combination with drugs of the related art in terms of treatment of cancer, the peptide of the present invention selectively delivers a drug only to a cancer tissue and a cancer cell, so that drug efficacy may be increased while drug side effects on a normal tissue may be significantly reduced at the same time.

For use as the drug, any anticancer drug that is conventionally used in the treatment of cancer can be used so long as the anticancer drug is able to be linked to the peptide of the present invention. Examples of the drug include cisplatin, 5-fluorouracil, adriamycin, methotrexate, vinblastine, busulfan, chlorambucil, cyclophosphamide, melphalan, nitrogen mustard, nitrosourea, taxol, paclitaxel, docetaxel, 6-mercaptopurine, 6-thioguanine, bleomycin, daunorubicin, doxorubicin, epirubicin, idarubicin, mitomycin-C, and hydroxyurea. In addition, the linking of the anticancer drug to the peptide of the present invention may be performed by a method known in the art, for example, covalent bonding, cross linking, or the like. For this purpose, the peptide of the present invention may be, if necessary, subjected to chemical modifications to the extent that the activity thereof is not lost.

MODE OF THE INVENTION

Hereinafter, to promote understanding of one or more exemplary embodiments, reference has been made in detail to embodiments. The present invention, however, may be embodied in many different forms and should not be construed as being limited to the exemplary embodiments set forth herein. Rather, these embodiments are provided so that this disclosure will be thorough and complete, and will fully convey the scope of the present invention to one of ordinary skill in the art.

<Example 1> Establishment of a Mouse Model Transplanted with a Patient's Colorectal Cancer Tissue In order to reproduce patient's cancer microenvironments as similar as possible, a cancer tissue extracted from an actual patient having colorectal cancer was transplanted into a mouse, thereby establishing an animal model most similar to a patient having cancer. Accordingly, an ideal animal model of cancer that has overcome limitations that existing animal models transplanted with cultured cancer cells had was obtained.

Regarding the establishment of such an animal model transplanted with a patient's colorectal cancer tissue, the cancer tissue extracted from a patient was cultured in an NOD/SC ID mouse. Once the cancer tissue was found in the NOD/SCID mouse, subculturing was carried out by using a Balb/c nude mouse, beginning from the next subculturing. All experiments related to the establishment of the corresponding mouse model were carried out after approval under the strict regulations by of the Clinical Research Ethics Committee of the Asan Medical Center and the Ethics Committee for Animal Experiments of the Asan Institute for Life Science. In addition, the patient's cancer tissue was distributed from the Bio Research Center (BRC) of the Asan Medical Center via a regulated route.

Then, the distributed cancer tissue was kept in a specific preservative solution and transferred directly to an animal chamber, so as to maintain a state in which the cancer tissue was not separated from a patient yet. After an NOD/SCID mouse was anesthetized via intraperitoneal injection of anesthetics, the cancer tissue was cut into pieces each having a size of 3×3 mm. Next, each of both flanks of the NOD/SCID mouse was transplanted with a piece of the cut cancer tissues, and sutured. The NOD/SCID mouse was then recovered on a heating pad for about 2 hours (conditions of the preservative solution: HBSS containing 100 IU/ml penicillin, 100 μg/ml streptomycin, 100 μg/ml gentamicin, 2.5 μg/ml amphotericin B, and 5% fetal bovine serum). After completion of the transplantation, the NOD/SCID mouse was raised until tumors were formed. Meanwhile, the formation and growth of tumors were checked at least once a week. When the transplanted cancer tissues grew to a size of at least 500 mm³, an extraction process was performed thereon. Then, the extracted cancer tissues were each cut into pieces each having a size of 3×3 mm for subculturing. A nude mouse was anesthetized via intraperitoneal injection of anesthetics, and a piece of the cut cancer tissues was transplanted subcutaneously on the right thigh of the nude mouse. A transplantation site was changed from the flank to the thigh so that irradiation can be locally done without affecting other organs during irradiation. That is, a finally used mouse model transplanted with a patient's colorectal cancer tissue in the present invention was a mouse model established in a way that a cancer tissue that underwent subculturing four times was re-transplanted to form a cancer tissue. When the size of the cancer tissue was increased to about 250 mm³, only the cancer tissue was irradiated with 2 grays (Gy) of radiation. After having recovery time for no longer than 24 hours, in vivo peptide screening was performed. Here, a non-irradiated population, which is a control group, was also subjected to screening in a separate manner. The establishment of such a mouse model was performed in the same manner for two colorectal cancer tissues, and the results thereof are shown in FIG. 1.

<Example 2> Verification and Classification of Radioresponsiveness of the Mouse Model In order to complete drawing of growth curves of distinct cancer after the formation of tumor was confirmed in the mouse transplanted with the patient's cancer tissue, two different animal models transplanted with the patient's colorectal cancer tissue were prepared so that growth curves of cancer were obtained from each of the two different animal models. The growth curves obtained therefrom were then utilized as the standard for control groups of an invention in the future. Here, the tumor size was measured by using a caliper every 2-3 days, and the resulting measurement value was substituted in a formula for calculating the tumor volume, thereby drawing the growth curves (Formula for calculating tumor size: Tumor volume=$a^2b/2$ (a: a short diameter of tumor, b: a long diameter of tumor)).

For each patient case, 6 subcultured (P3) nude mice were prepared to be divided into two groups of three mice, and an experiment was carried out with an irradiated population and a non-irradiated population as a control group. When the tumor size was increased up to 100 mm³, the right hind leg of the mouse where tumor was formed was irradiated with 2 Gy of radiation. Beginning from the first day after the irradiation, the tumor size was measured until it was increased up to about 1,000 mm³, thereby plotting the tumor volume and completing drawing the growth curves. Based on these results and depending on the sensitivity to the radiotherapy, patient cases were classified into radio-sensitive patient groups (also known as case C87) and radio-resistant cases (also known as case C65). The irradiation was performed by using a 6 MV photon beam linear accelerator (CL/1800, Varian, Calif., USA) and a 1 cm bolus. The corresponding results of the above contents are shown in FIG. 2.

<Example 3> In Vivo Peptide Screening—M13 Phage Display

Regarding the mouse model transplanted with the patient's colorectal cancer tissue and classified depending on the radio-sensitivity in Example 2, a method for identifying a peptide having high specificity during in vivo peptide screening using a random loop peptide library was designed. For use as the library, a loop peptide library manufactured to have about 2.7 billion different amino acids sequences via random array of 7 amino acids [(i.e., a library fused with an M13 phage gp3 minor coat protein)-Ph.D™ phage display peptide library kit, New England Biolabs (NEB)] was purchased. To screen a peptide showing specific binding in each of the irradiated population (2 groups) and the control group (2 groups) of the established mouse model, a M13 phage peptide library was injected into the tail vein of the mouse so that the M13 phage peptide library was circulated in vivo through the tail vein of the mouse (also known as a method of binding an in vivo cancer tissue with an M13 phage peptide library). Then, a peptide-expressing phage specifically binding to the cancer tissue only was selected, and such a screening scheme is shown in FIG. 3. In detail, FIG. 3 shows an M13 phage screening scheme for screening a cancer tissue-targeting peptide, wherein (1) a mouse model in which a cancer tissue was formed on the right thigh was established, (2) a phage library in which a loop peptide library consisting of 7 amino acids was expressed on a surface of a M13 phage was injected into the tail vein of the mouse to allow in vivo circulation of the phage library for 15 minutes, (3) undesired phages were washed (also known as perfusing), and (4) the cancer tissue was finally extracted and homogenized to elute phages bound with the cancer tissue. The eluted phages infected *Escherichia coli*, and through amplification of the phages and counting of the number of the phages (also known as titering), the resulting phages were injected again into the tail vein of the mouse to allow in vivo circulation. By repeating such cycles, the number of repetition also increased, and accordingly, a process of screening phages that were gradually specific to the cancer tissue and showed a strong binding strength was performed (also known as biopanning). Biopanning was finally performed three times in total so that a phage expressing a sequence of a peptide specifically binding to the patient's in vivo colorectal cancer tissue was obtained. In addition, to confirm whether the peptide-expressing phage selected above targeted the cancer tissue only, other in vivo organs were also subjected to comparison. That is, for every biopanning, phages were eluted from each of extracted heart, lung, liver, spleen, kidney, and cancer tissue, and the phage concentration was measured for comparison. The results of the comparison are shown in FIG. 4. Finally, the obtained phages infected *E. coli* ER2738 cells that are host cells, and were subjected to amplification in an LB medium. Then, 100 phage plaques were selected randomly, and the M13 phage genomic DNA (single-stranded circular DNA) was separated and purified to identify a gene sequence, thereby identifying an amino acid sequence of a peptide expressed in a phage-surface protein (e.g., a gp3 minor coat protein) and targeting the cancer tissue. The same procedures were carried out on each of the irradiated group (2 groups) and the control group (2 groups) of Example 2 in terms of the in vivo peptide screening. The Clustal W program for sequence analysis was used to summarize peptide sequences, and the results are shown in Tables 1 and 2.

TABLE 1

| Patient case | Irradiation | No. | Peptide sequence |
|---|---|---|---|
| Radio-resistant colorectal cancer tissue of patient (case C65) | Non-irradiated population | A1 | SHMEYPR (SEQ ID NO: 1) |
| | | A2 | NTGSPYE (SEQ ID NO: 2) |
| | | A3 | SNVYDHN (SEQ ID NO: 3) |
| | | A4 | STEHTRS (SEQ ID NO: 4) |
| | | A5 | SWGDRIL (SEQ ID NO: 5) |
| | | A6 | LQPKASQ (SEQ ID NO: 6) |
| | | A7 | ASKSTHD (SEQ ID NO: 7) |
| | | A8 | DVSGNW (SEQ ID NO: 8) |
| | | A9 | DLLHRGA (SEQ ID NO: 9) |
| | | A10 | MARYMSA (SEQ ID NO: 10) |
| | | A11 | NTWMKSK (SEQ ID NO: 11) |
| | Irradiated population | B1 | STMNGKV (SEQ ID NO: 12) |
| | | B2 | SHMEYPR (SEQ ID NO: 1) |
| | | B3 | TVRSSAE (SEQ ID NO: 13) |
| | | B4 | VPSQKSK (SEQ ID NO: 14) |
| | | B5 | TPSFSKI (SEQ ID NO: 15) |
| | | B6 | GYSSFNR (SEQ ID NO: 16) |
| | | B7 | LKLGEKW (SEQ ID NO: 17) |

TABLE 2

| Radio-sensitive colorectal cancer tissue of patient (case C87) | Non-irradiated population | E1 | SHMEYPR (SEQ ID NO: 1) |
|---|---|---|---|
| | | E2 | GYSSFNR (SEQ ID NO: 16) |
| | | E3 | NTGSPYE (SEQ ID NO: 2) |
| | | E4 | VQMPAHS (SEQ ID NO: 18) |
| | | E5 | GGNSNQR (SEQ ID NO: 19) |
| | | E6 | TAFSLGK (SEQ ID NO: 20) |
| | | E7 | QQTKNYY (SEQ ID NO: 21) |
| | | E8 | AIKNTKS (SEQ ID NO: 22) |
| | | E9 | TVRTSAV (SEQ ID NO: 23) |

TABLE 2-continued

|  |  |  |  |
|---|---|---|---|
|  | E10 | LTGSVNK | (SEQ ID NO: 24) |
|  | E11 | MNFIQKN | (SEQ ID NO: 25) |
|  | E12 | DETSGQI | (SEQ ID NO: 26) |
|  | E13 | KISLPHN | (SEQ ID NO: 27) |
|  | E14 | AFKSPSG | (SEQ ID NO: 28) |
|  | E15 | LKTSGTY | (SEQ ID NO: 29) |
|  | E16 | RSTGSSC | (SEQ ID NO: 30) |
|  | E17 | YVSKNNS | (SEQ ID NO: 31) |
|  | E18 | HKTEHRS | (SEQ ID NO: 32) |
| Irradiated population | F1 | KLTQMM | (SEQ ID NO: 33) |
|  | F2 | LKLGEKW | (SEQ ID NO: 17) |
|  | F3 | SFFPFST | (SEQ ID NO: 34) |
|  | F4 | DNSKLVE | (SEQ ID NO: 35) |
|  | F5 | QLWQKEQ | (SEQ ID NO: 36) |
|  | F6 | NTGSPYE | (SEQ ID NO: 2) |
|  | F7 | LGSVGRD | (SEQ ID NO: 37) |
|  | F8 | GQSGARF | (SEQ ID NO: 38) |
|  | F9 | NGNSNTL | (SEQ ID NO: 39) |
|  | F10 | TNPYPLD | (SEQ ID NO: 40) |

<Example 4> In Vivo Imaging for Confirming Targeting Ability of a Discovered Peptide Regarding a Patient's Colorectal Cancer Tissue To verify whether the obtained phage expressing a loop peptide has targeted the in vivo transplanted cancer tissue and to confirm targeting efficiency of the obtained phage, in vivo imaging was performed.

In detail, regarding in vivo imaging verification, the peptide-expressing phage was amplified, and a process of linking a fluorescent probe (Cy5.5) was performed. In particular, 1 μg/μl of N-hydroxysuccinimide esters of Cy5.5 (Amersham) was added to 1 mL of bicarbonate buffer (pH 8.3) having the phage concentration of $10^{12}$ plaque forming units (pfu), and then, in a condition where a dark environment was maintained, a phage-surface protein was linked to the Cy5.5 fluorescent probe at room temperature for 3 hours. That is, amine groups of the phage-surface protein were chemically linked to N-hydroxysuccinimide esters of the Cy5.5 fluorescent probe via a covalent bond. The peptide-expressing phages to which the Cy5.5 fluorescent probe was linked were each obtained by precipitation with 170 μl of 20% (w/v) PEG 8000/2.5 M NaCl solution and purification. To determine a proportion of the Cy5.5 fluorescent probe linked to each of the finally obtained phage samples, an IVIS spectrum imaging system (Xenogen) was used for measurement, and region of interest (ROI) values were determined using the software program of a corresponding device. Accordingly, it was confirmed that the Cy5.5 fluorescent probe was linked to each of the phage samples at almost the same linking proportion.

After each of the prepared phage samples was injected into the mouse model of Example 1 through the vein tail of the mouse, images thereof were measured once a day immediately after the injection, thereby confirming in vivo circulation and discharge process of the peptide-expressing phage. Although there were difference in populations, the images were measured from the last $7^{th}$ day to the last $11^{th}$ day, thereby screening the peptide-expressing phage verified to target the cancer tissue only. In addition, on the last day of the in vivo imaging, the cancer tissues were each extracted, to thereby obtain ex vivo images thereof. The results are shown in FIG. 5.

To compare the targeting efficiency of the peptide-expressing phage selected from each population based on the results of FIG. 5, the pieces of the extracted cancer tissue were collected independently, and phages bound to the cancer tissues were eluted. The concentration of the eluted phages was measured as well as the weight of each cancer tissue in terms of establishing numerical standardization. In this regard, the concentration of the phages relative to the weight of the cancer tissue was calculated and quantified. In addition, to quantify the results obtained from the in vivo imaging and the ex vivo imaging according to the fluorescence intensity, ROI values were calculated to obtain total flux values. Each of the values being calculated and quantified was standardized by comparing the control group with the mouse injected by processing a Cy5.5 probe with a phage-free Cy5.5 dye and an empty phage where a peptide was not expressed. The results are shown in Tables 3 and 4. Based on these results of Tables 3 and 4, peptide sequences each having 4 different sequences were selected in each population. When compared with sequences of other peptide-expressing phages, it was confirmed that the selected peptides had excellent targeting ability.

TABLE 3

| Patient case | Irradiation | Sample | pfu/mg | in vivo ROI | ex vivo ROI |
|---|---|---|---|---|---|
| Radio-resistant colorectal cancer tissue of patient (case C65) | Non-irradiated population | Cy5.5 | — | 1.00 | 1.00 |
|  |  | Empty | 0.23 | 1.43 | 1.16 |
|  |  | A1 | 136.36 | 1.77 | 1.27 |
|  |  | A2 | 181.48 | 2.04 | 1.61 |
|  |  | A3 | 34.8 | 1.62 | 0.67 |
|  |  | A4 | 264.86 | 3.20 | 1.83 |
|  |  | A5 | 51.38 | 2.16 | 1.52 |
|  |  | A6 | 15.4 | 2.75 | 1.47 |
|  |  | A7 | 27.14 | 1.80 | 1.08 |
|  |  | A8 | 8.56 | 2.99 | 1.57 |
|  |  | A9 | 54.17 | 2.35 | 0.56 |
|  |  | A10 | 183.16 | 2.26 | 1.58 |
|  |  | A11 | 6.71 | 1.93 | 0.95 |
|  | Irradiated population | Cy5.5 | — | 1.00 | 1.00 |
|  |  | Empty | — | 1.40 | 0.72 |
|  |  | B1 | 16.67 | 1.52 | 1.48 |
|  |  | B2 | 230 | 2.27 | 1.89 |
|  |  | B3 | 195.40 | 2.38 | 1.63 |

TABLE 3-continued

| Patient case | Irradiation | Sample | pfu/mg | in vivo ROI | ex vivo ROI |
|---|---|---|---|---|---|
| | | B4 | 20.62 | 2.12 | 1.36 |
| | | B5 | 209.47 | 4.07 | 2.43 |
| | | B6 | 211.76 | 3.03 | 2.06 |
| | | B7 | 3.45 | 1.72 | 0.62 |

TABLE 4

| Patient case | Irradiation | Sample | pfu/mg | in vivo ROI | ex vivo ROI |
|---|---|---|---|---|---|
| Radio-sensitive colorectal cancer tissue of patient (case C87) | Non-irradiated population | Cy5.5 | — | 1.00 | 1.00 |
| | | Empty | 1.40 | 1.21 | 0.82 |
| | | E1 | 74.12 | 1.68 | 1.72 |
| | | E2 | 3.96 | 1.12 | 0.62 |
| | | E3 | 1.55 | 1.13 | 0.77 |
| | | E4 | 5.00 | 0.84 | 0.94 |
| | | E5 | 15.96 | 0.92 | 0.76 |
| | | E6 | 4.24 | 0.78 | 0.77 |
| | | E7 | 58.32 | 2.02 | 1.38 |
| | | E8 | 15.00 | 0.90 | 0.49 |
| | | E9 | 86.40 | 1.27 | 1.20 |
| | | E10 | 2.25 | 1.19 | 1.00 |
| | | E11 | 4.43 | 1.05 | 0.34 |
| | | E12 | 5.56 | 1.24 | 1.07 |
| | | E13 | 1.22 | 1.50 | 0.93 |
| | | E14 | 2.89 | 0.70 | 0.55 |
| | | E15 | 6.13 | 0.77 | 0.47 |
| | | E16 | 2.14 | 0.50 | 0.24 |
| | | E17 | 204.00 | 1.66 | 1.29 |
| | | E18 | 4.15 | 0.69 | 0.21 |
| | Irradiated population | Cy5.5 | — | 1.00 | 1.00 |
| | | Empty | 8.18 | 0.96 | 0.83 |
| | | F1 | 6.73 | 1.63 | 2.39 |
| | | F2 | 1.90 | 1.00 | 2.92 |
| | | F3 | 22.31 | 1.07 | 2.64 |
| | | F4 | 69.18 | 1.59 | 3.11 |
| | | F5 | 144.55 | 1.63 | 3.72 |
| | | F6 | 4.75 | 1.15 | 2.64 |
| | | F7 | 141.04 | 1.61 | 3.97 |
| | | F8 | 6.10 | 1.18 | 1.92 |
| | | F9 | 95.24 | 1.77 | 4.45 |
| | | F10 | 7.86 | 1.91 | 1.74 |

<Example 5> In Vivo Imaging for Screening a Radio-Sensitive Target Peptide

Among the various peptide-expressing phages selected from the above, the in vivo imaging was attempted again for a B5 peptide, which is a peptide sequence screened only from the irradiated population in the radio-resistant case (case C65). At the same time, to confirm the responsiveness in control groups other than the population of interest, a crossover experiment was carried out. In detail, in the presence of differences in irradiation between the radio-sensitive case and the radio-resistant case of Example 1, the in vivo imaging was carried out to determine the targeting of the B5 peptide sequence in 4 populations in total. Here, the irradiated population of case C65 was set as an experimental group while the non-irradiated population of case C65 and all the populations of case C87 were set as control groups. In the same manner as in Example 4, peptide-expressing phages were amplified and a process of linking a Cy5.5 fluorescent probe was carried out. Then, through the tail vein injection in each population, images thereof were observed until the end of the last 7$^{th}$ day. Consequently, when compared with a population in which injection was made by processing a Cy5.5 probe with a phage-free Cy5.5 dye and an empty phage where a peptide was not expressed, it was confirmed that only the irradiated population of the radio-resistant case (case C65) has exhibited excellent targeting ability. FIG. 6 shows the results of the present embodiment, and FIG. 7 shows the results of standardization of ROI values. Consequently, regarding the B5 peptide sequence, it was confirmed that the B5 peptide sequence may be a sequence that targets a factor (e.g., a biomarker) inducing resistance against radiation during radiotherapy, and in other words, the B5 peptide sequence may be a sequence that was responsive to cancer microenvironments influenced by irradiation.

<Example 6> Histological Verification of a Peptide for Tracing a Radio-Resistant Factor To verify histological targeting ability of the B5 peptide sequence verified in Example 5, the imaging of the B5 peptide sequence was obtained. Then, cancer tissues of each population were extracted to prepare paraffin blocks and slices. In detail, (1) the extracted cancer tissues were immersed in a formaldehyde solution at room temperature for 24 hours in terms of for immobilization. Then, following a dehydration process, paraffin was added to the solution through penetration to form paraffin blocks. Afterwards, a microtome was used to manufacture slices having a thickness of 3 μm. To perform real immunohistological staining, (2) following a deparaffinization process performed on the slices, (3) an unmasking process was performed so that structures of various proteins immobilized to the tissue slices were recovered to restore sites where antibodies normally bind. Sequentially, (4) a blocking process was performed using a 5% BSA solution, (5) primary antibodies were bound (wherein the antibodies used herein were anti-mouse M13 IgG recognizing M13 phage capsid proteins), (6) and secondary antibodies were bound while HRP was bound. Afterwards, (7) sites where phages were present were stained using DAB development, (7) the nuclei of the phages were stained with hematoxylin, and (8) a dehydration process was performed thereon. Once completed, mounting was performed so that the tissue slices that were immunohistochemically stained were permanently preserved. The results of immunohistochemical staining performed as described above are shown in FIG. 8. The results of FIG. 7 clearly confirm that the B5 peptide sequence of Example 5 specifically bound only to the irradiated population in the radio-resistant colorectal cancer patient case (C65).

<Example 7> Verification of Selective Targeting Ability of a Peptide for Tracing a Radio-Resistant Factor in a Colorectal Cancer Tissue of Other Patients To confirm whether the selected B5 peptide having the ability to trace the radio-resistant factor exhibited the same targeting ability in a patient's radio-resistant colorectal tissue other than the patient's colorectal tissue used in the screening above, the B5 peptide was applied to a mouse transplanted with other colorectal cancer tissues of a patient. In detail, by extending the crossover experiment verified in Example 4, radio-sensitive case 1 and radio-resistant case 1 regarding other colorectal cancer tissues of a patient characterized as adenocarcinoma were introduced in addition to the radio-sensitive case and the radio-resistant case of Example 1. In the same manner as in Example 4, the B5 peptide-expressing phages were amplified and a process of linking a Cy5.5 fluorescent probe was carried out. Regarding the confirmation of the targeting ability of the B5 peptide, the in vivo imaging was used for observation in the same manner as in Example 5. Consequently, it was confirmed that the radio-sensitive colorectal cancer tissue did not show any targeting ability regardless of irradiation, and that the radio-resistant colorectal cancer tissue exhibited targeting ability only in the case of irradiation. FIG. 9 shows the results of the present embodiment. In detail, the targeting ability of the B5 peptide sequence targeting a factor inducing resistance against radiation during radiation therapy in Example 6 was also verified in other colorectal cancer tissues of a radio-resistant patient, thereby confirming the possibility of the B5 peptide sequence as a sequence that is responsive to cancer microenvironments causing induction of resistivity during radiotherapy on colorectal cancer. However, in the patients having radio-sensitive colorectal cancer, it was clearly confirmed that the B5 peptide sequence, as a peptide sequence showing no targeting ability regardless of irradiation, was a sequence selectively tracing a radio-resistant factor. Ultimately, it was verified that the targeting ability of the B5 peptide sequence was not limited to the radio-resistant case including specific patients having colorectal cancer, but was rather applicable to other colorectal cancer tissues of a radio-resistant patient. In this regard, the limited range of application in clinical applications was overcome.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

The invention claimed is:

1. A method for diagnosing colorectal cancer, comprising:
 applying a composition comprising the peptide of SEQ ID NO: 15 to a patient of having a colorectal cancer; and
 identifying the presence of the colorectal cancer.

2. A method for diagnosing radio-sensitive colorectal cancer, comprising:
 applying a composition comprising a peptide comprising one of the amino acid sequences selected from the group consisting of SEQ ID NOs: 12 to 15, 17, and 33 to 40 to a patient having a colorectal cancer; and
 identifying the presence of the radio-sensitive colorectal cancer.

3. The method of claim 1, wherein the peptide is labeled with one selected from the group consisting of a chromogenic enzyme, a radioactive isotope, a chromopore, and a luminescent or fluorescent material.

4. A method for diagnosing prognosis of colorectal cancer that is influenced by irradiation, comprising:
 applying a composition comprising a peptide comprising one of the amino acid sequences selected from the group consisting of SEQ ID NOs: 12 to 15, 17, and 33 to 40 to a patient having a colorectal cancer; and
 determining the prognosis of colorectal cancer that is influenced by the irradiation.

5. The method of claim 4, wherein the diagnosis of prognosis of colorectal cancer that is influenced by irradiation is determined by radio-resistance or radio-sensitivity.

6. A method for diagnosing colorectal cancer, comprising:
 obtaining a colorectal cancer tissue sample from a patient;
 transplanting the tissue sample into a subject;
 applying a composition comprising the peptide of SEQ ID NO: 15 to the subject; and
 identifying the presence of the colorectal cancer.

7. A method for diagnosing radio-sensitive colorectal cancer, comprising:
 obtaining a colorectal cancer tissue sample from a patient;
 transplanting the tissue sample into a subject;
 applying a composition comprising a peptide comprising one of the amino acid sequences selected from the group consisting of SEQ ID NOs: 12 to 15, 17, and 33 to 40 to the subject; and
 identifying the presence of the radio-sensitive colorectal cancer.

8. The method of claim 6, wherein the peptide is labeled with one selected from the group consisting of a chromogenic enzyme, a radioactive isotope, a chromopore, and a luminescent or fluorescent material.

9. A method for diagnosing prognosis of colorectal cancer that is influenced by irradiation, comprising:
 obtaining a colorectal cancer tissue sample from a patient;
 transplanting the tissue sample into a subject;
 applying a composition comprising a peptide comprising one of the amino acid sequences selected from the group consisting of SEQ ID NOs: 12 to 15, 17, and 33 to 40 to the subject; and
 determining the prognosis of colorectal cancer that is influenced by the irradiation.

10. The method of claim 9, wherein the diagnosis of prognosis of colorectal cancer that is influenced by irradiation is determined by radio-resistance or radio-sensitivity.

\* \* \* \* \*